(12) United States Patent
Shah

(10) Patent No.: US 11,872,599 B2
(45) Date of Patent: Jan. 16, 2024

(54) DENUDER

(71) Applicant: Medtronic Advanced Energy LLC, Minneapolis, MN (US)

(72) Inventor: Raza U. Shah, Minneapolis, MN (US)

(73) Assignee: MEDTRONIC ADVANCED ENERGY LLC, Minneapolis, MN (US)

(*) Notice: Subject to any disclaimer, the term of this patent is extended or adjusted under 35 U.S.C. 154(b) by 248 days.

(21) Appl. No.: 17/509,617

(22) Filed: Oct. 25, 2021

(65) Prior Publication Data

US 2022/0040740 A1 Feb. 10, 2022

Related U.S. Application Data

(62) Division of application No. 16/508,458, filed on Jul. 11, 2019, now Pat. No. 11,154,912.

(60) Provisional application No. 62/703,250, filed on Jul. 25, 2018.

(51) Int. Cl.
*A61F 2/00* (2006.01)
*B08B 3/02* (2006.01)
*A61F 2/46* (2006.01)
*B05B 1/26* (2006.01)

(52) U.S. Cl.
CPC .............. *B08B 3/02* (2013.01); *A61F 2/4644* (2013.01); *A61F 2/4675* (2013.01); *B05B 1/262* (2013.01); *A61F 2002/4646* (2013.01)

(58) Field of Classification Search
CPC .......... B08B 3/02; A61F 2/4644; B05B 1/262
USPC .......................................................... 452/135
See application file for complete search history.

(56) References Cited

U.S. PATENT DOCUMENTS

| | | | |
|---|---|---|---|
| 3,314,659 A | 4/1967 | Ranson | |
| 6,402,070 B1 | 6/2002 | Ishida et al. | |
| 6,484,954 B2 | 11/2002 | Lenox | |
| 6,824,087 B2 | 11/2004 | McPherson et al. | |
| 7,131,605 B2 | 11/2006 | McPherson et al. | |
| 7,569,245 B2* | 8/2009 | Kang | A23L 13/60 210/806 |
| 8,002,774 B2 | 8/2011 | Burmeister et al. | |
| 8,662,967 B1* | 3/2014 | Blanchard | A22C 17/004 452/138 |
| 8,740,114 B2 | 6/2014 | Koltz et al. | |
| 9,693,844 B1* | 7/2017 | Karapetyan | A61C 19/002 |
| 2007/0164137 A1 | 7/2007 | Rasekhi | |
| 2011/0017241 A1* | 1/2011 | Cantrell | A47L 15/0092 134/184 |
| 2014/0263778 A1 | 9/2014 | Koltz et al. | |
| 2014/0303623 A1 | 10/2014 | Diehl et al. | |

FOREIGN PATENT DOCUMENTS

DE 202004017681 U1 9/2005
EP 619722 B1 7/2001
(Continued)

*Primary Examiner* — Richard T Price, Jr.
(74) *Attorney, Agent, or Firm* — Fletcher Yoder P.C.

(57) ABSTRACT

A method of denuding bone stock with a denuder, such as a bone stock denuder container, is disclosed. The bone stock is deposited into a wash chamber formed with a curved chamber wall. The bone stock is impacted with a stream of fluid under pressure to separate non-bone tissue from bone. Fluid and non-bone tissue are drained from the wash chamber.

20 Claims, 2 Drawing Sheets

(56) References Cited

FOREIGN PATENT DOCUMENTS

EP    2907482 B1   8/2017
WO    9605914 A1   2/1996

* cited by examiner

DENUDER

CROSS-REFERENCE

This Non-Provisional Utility application is a Divisional of U.S. patent application Ser. No. 16/508,458, filed Jul. 11, 2019, which claims benefit to U.S. Provisional Application No. 62/703,250, filed Jul. 25, 2018, entitled "DENUDER," which is incorporated herein by reference.

BACKGROUND

This disclosure relates generally to the field of medical devices and systems to clean bone stock for medical use such as in surgical procedures. Such medical devices may be referred to by a number of names including denuders and bone denuders that are configured to remove non-bone tissue including muscle, periosteum, and connective tissue from bone. Bone that is substantially free from non-bone tissue may be referred to as denuded bone.

Pieces of bone can be used in various medical and surgical procedures. For example, bone pieces can be used for spinal fusion, to repair defects caused by trauma, in autograft transplant surgery, or for storage in a tissue bank such as for research or allograft transplants. In an example spinal fusion procedure, a compound formed out of milled bone can be placed around implanted support rods to hold adjacent vertebrae in alignment. The compound serves as a lattice upon which tissues forming a vertebra grow so as to form a foundation around the rods. Bone pieces can also be used as filler or for a growth formation lattice in orthopedic surgical procedures and other procedures such as maxillofacial procedures. Often, the preferred source of bone stock for bone pieces is the patient themselves, because the patient's immune system is less likely to reject patient's bone than a donor bone.

Several steps are taken in order to prepare bone pieces for use in a medical or surgical procedure. In an example procedure, a tissue sample of bone stock is surgically removed, or harvested, from the patient. After removal of the bone stock from the patient, non-bone tissue is removed from the bone. The denuded bone is often subjected to further processing such as bone milling to form appropriate sized bone pieces. The bone pieces can be surgically transplanted into another portion of the patient.

Current approaches to remove the non-bone tissue from the bone can be time consuming, labor intensive and hazardous to healthcare personnel (e.g., cutting through gloves). In one example, a clinician grasps the bone stock with one hand and uses a scalpel, curette, or rongeur with the other hand to remove non-bone tissue from bone. Hand removal of the non-bone tissue using such surgical tools can take over a half an hour of work and is prone to clinician fatigue and possible injury.

SUMMARY

This summary is provided to introduce a selection of concepts in a simplified form that are further described below in the Detailed Description.

The disclosure includes examples of a denuder system, a denuder container, and methods of use. The denuder system includes a denuder container operably coupled to a source of fluid under pressure. The denuder container is configured to receive a bone stock into a wash chamber and includes a nozzle operably coupleable to the source of fluid under pressure to deliver a fluid stream into the wash chamber. the denuder container includes a curved chamber wall to form the wash chamber. In one example, the curved chamber wall includes a curvilinear cross section in the plane of the fluid stream. The configuration of the wash chamber and the placement of the fluid stream are selected to remove non-bone tissue from the bone stock and expose multiple sides of the bone stock to the fluid stream. Non-bone tissue and fluid are drained from the wash chamber via waste openings in the denuder container.

In one aspect, the disclosure includes an example of a denuder container having a nozzle and a container body. The nozzle is configured to be fluidically coupled to a source of fluid and to direct a fluid stream. The container body includes a curved chamber wall that forms a wash chamber. The wash chamber is configured to receive a bone stock, and the nozzle is configured to direct the fluid stream to impact the curved chamber wall.

In another aspect the disclosure includes an example of a denuder container. The denuder container includes a nozzle configured to be fluidically coupled to a source of fluid and to direct a fluid stream. The denuder container also includes a curved chamber wall that forms a wash chamber. The wash chamber is configured to receive a bone stock, and the nozzle is configured to direct the fluid stream to impact the curved chamber wall. The denuder container also includes a redirection wall that forms a redirection chamber. A grate is included in the curved chamber wall between the redirection chamber and the wash chamber such the redirection chamber is in fluid communication with the wash chamber.

In another aspect the disclosure includes an example of a method of denuding bone stock. The bone stock is deposited into a wash chamber formed with a curved chamber wall. A stream of fluid under pressure impacts the bone stock to separate non-bone tissue from bone. The fluid and non-bone tissue are drained from the wash chamber.

DETAILED DESCRIPTION

Figure 1:
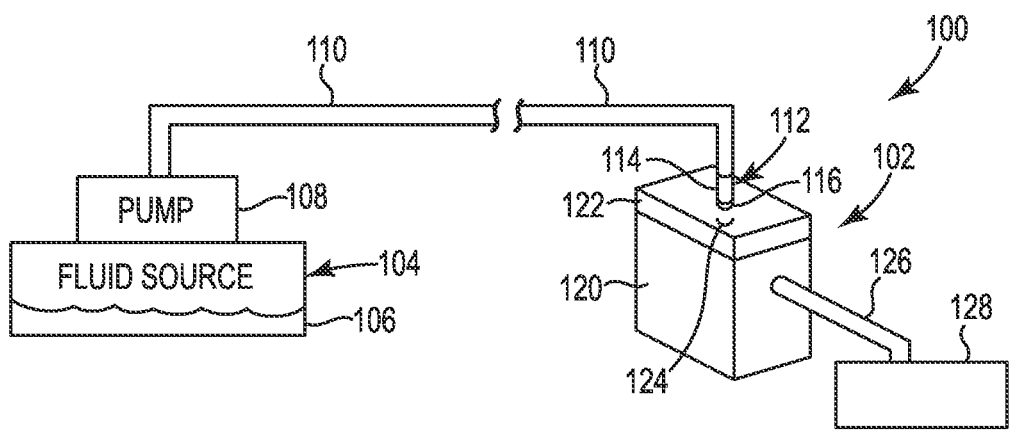
FIG. 1 is a schematic view illustrating an example denuder of the disclosure having a denuder container.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive.

FIG. 1 illustrates an example denuder system 100. The denuder system 100 includes a denuder container 102 into which bone stock can be placed. The denuder system 100 includes a fluid source 104 that includes a fluid 106 such as a liquid including sterile water or saline. In some examples, the fluid can include an additive such as a biocompatible abrasive or detergent, which may be mixed into the fluid 106 at the fluid source 104 or elsewhere in the denuder system 100. In one example, the additive can be dry ice, or a solid form of carbon dioxide. The denuder system 100 includes a pump 108 operably coupled to the fluid source 104 to draw the fluid 106 and deliver the fluid to the denuder container 102 via a conduit such as tube 110 in fluid communication with the pump 108 and the denuder container 102. In one example, the pump 108 delivers the fluid under a pressure as a pressurized fluid, such as at a level of about 100 to 100,000 pounds per square inch, or 689.47 kPa-689.47 MPa, and the tube 110 is a high-pressure hose. The tube 110, in fluid communication with the denuder container 102, is operably coupled to the denuder container 102 via a coupling 112 such as quick connect coupling (sometimes referred to as a quick disconnect or quick release fitting or coupling) or other generally fluid-tight seal such as flanged connections or threaded connections. In one example, the tube 110 may be equipped with a fitting 114 to mate with a fitting 116 on the denuder container 102. The tube 110 may further include a self-sealing valve to contain any fluid 106 in the tube 110.

In the illustrated example, the denuder container 102 includes a container body 120 and a container cap 122. The container cap 122 attached to the container body 120 forms a generally fluid-tight seal around a chamber into which the bone stock is received. In the example, the container cap 122 includes the fitting 116 to receive the tube 110, and fluid 106 is introduced into the chamber via the container cap 122. Other examples are contemplated including the container body configured to receive the tube or the container cap oriented on the denuder container in configuration other than at the top. Examples of denuder container 102 having the container cap 122 forming the top of the denuder container 102 and including the fitting 116 configured to couple to the tube 110 is for illustration. The denuder container 102 includes a nozzle 124 within the chamber and in fluid communication with the fitting 116. In the example, the nozzle 124 is opposite the container cap 122 from the fitting 116. The nozzle 124 can create a selectively directed jet of fluid and sprays fluid into the chamber. In one example, the nozzle 124 sprays a generally fixed stream of fluid 106 into the chamber. In another example, the nozzle can create a moving stream of fluid 106, which may rotate or move laterally, within the chamber. In one example, the fluid stream is directed at a level of about 1,000 to 20,000 pounds per square inch, or 6.89-137.8 MPa, within the chamber. In one particular example, a fluid stream is directed at a level of about 2,000 pounds per square inch, or 13.8 MPa, to effectively denude bone. The fluid stream impinges against the bone stock to remove non-bone tissue from the bone. Fluid and non-bone tissue may be drained through a waste opening 126 on the denuder container 102. In some examples, dispelled fluid from waste opening is provided to a medical waste container for disposal. In another example, the dispelled fluid is recycled into the chamber via the denuder system 100.

During operation of the denuder system 100, bone stock is placed in the chamber within the denuder container 102. The container cap 122 is attached to the container body 120 to provide a fluid tight, or generally fluid tight seal. In one example, the container cap 122 is releasably locked to the container body 120. The denuder container 102 may include a gasket between the container body 120 and container cap 122 to help provide the fluid tight seal. The fitting 114 on the tube 110 is attached to the fitting 116 on the denuder container 102 and the tube 110 is coupled to the pump 108. A clinician can actuate the pump 108 with a switch, push button, or other actuator, and fluid 106 from the fluid source 104 is pumped into the denuder container 102 via nozzle 124 at high pressure. The pump 108 and tube 110 do not contact the bone stock or with fluid that has been in contact with the bone stock.

In one example, the pump 108 is operated for a selected cycle time. During this cycle time, the bone stock is denuded and clinicians do not contact the bone stock or the interior denuder container 102. The shape of the walls of the chamber as well as the direction of the fluid stream from the nozzle 124 for the non-bone tissue to separate from the bone. The shape of the walls of the chamber as well as the impingement of the fluid stream from the nozzle 124 against the bone stock causes the bone stock to tumble and move within the chamber to expose different sides to direct impingement of the fluid stream. This can facilitate separation and removal of non-bone tissue from the entire bone stock without intervention from a clinician. Without being bound to a particular theory of operation, direct impingement of the fluid stream from the nozzle, indirect impingement of the fluid stream after it collides with the walls of the chamber or the bone stock, and tumbling of the bone stock serves to remove the non-bone tissue from the bone. Waste fluid non-bone tissue can be dispelled from the chamber via waste opening 126, and can be collected in a drain 128 for appropriate disposal.

After the selected cycle time, which can be determined based on a number of factors including the size of the bone stock and the amount of non-bone tissue on the bone stock, the bone has been sufficiently denuded for further processing. In one example, the container cap 122 can be removed from the container body 120 and a clinician can remove the denuded bone from the chamber. In another example, the chamber can be joined with a bone mill in such a manner so as to allow the denuded bone to pass to the bone mill without manual intervention from the clinician.

Figure 2:
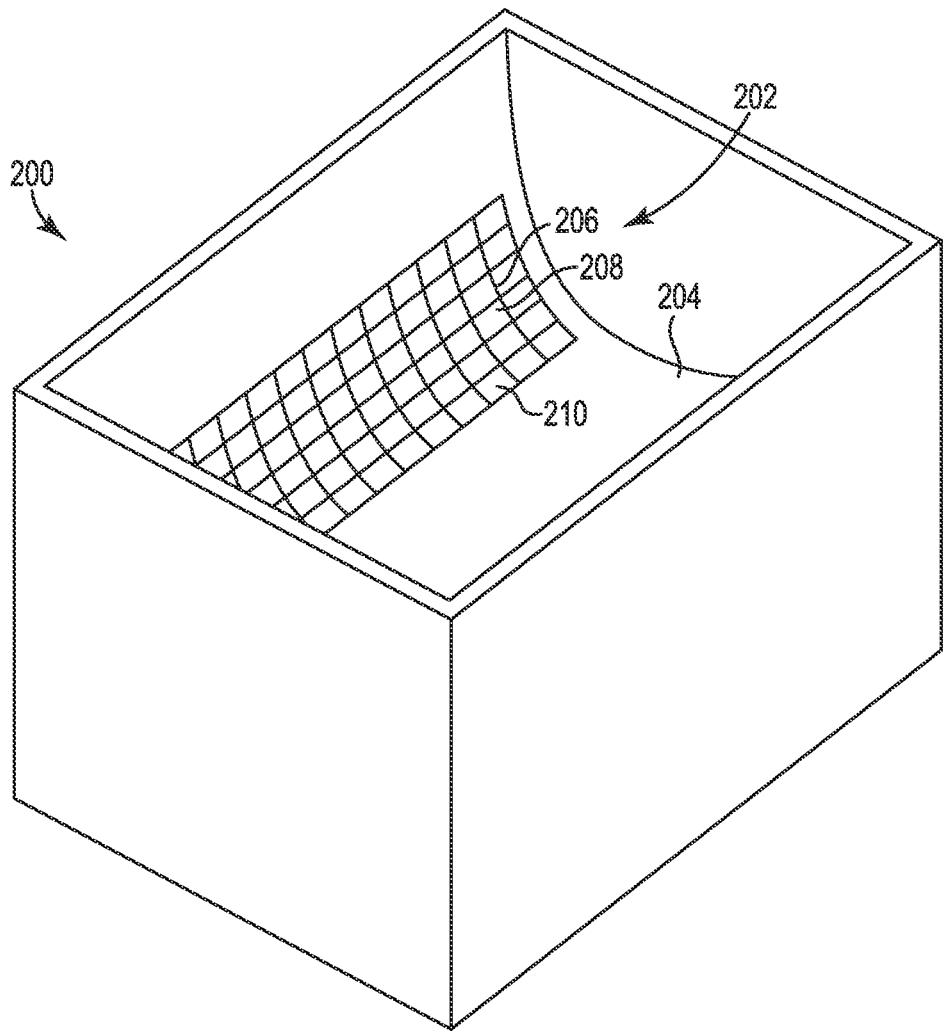
FIG. 2 is a schematic view illustrating a portion of an example denuder container of the example denuder of FIG. 1.

FIG. 2 illustrates an example portion of denuder container 200, which may correspond with denuder container 102 such as container body 120. A container cap, such as container cap 122 is removed and not shown to depict the interior of the denuder container 200. The example denuder container 200 includes a concave wash chamber 202 formed by chamber walls 204. A clinician can deposit bone stock into the wash chamber 202 where the bone stock is denuded with the fluid stream. In one example, the chamber walls 204 surrounding the wash chamber 202 can be generally solid save one or more waste openings 126 in the walls 204 through which the fluid is drained from the wash chamber 202. In another example, at least a portion of the chamber wall 204 can include a grate 206 over a redirection cavity 208, formed of a redirection channel wall 210, into which fluid can flow but the grate 206 is configured to hold the bone stock within the wash chamber 202. A fluid stream into the chamber 202 from the nozzle 124 can impinge against a chamber wall 204 and be directed through the grate 206 into the redirection cavity 208 where the fluid can contact the redirection channel wall 210 and be directed through the grate 206 and back into the wash chamber 202. The stream of fluid along such a path can impact the bone stock from one or more directions and cause the bone stock to tumble within the wash chamber 202, which can expose other surfaces of the bone stock to the stream of fluid.

In one example, the chamber walls 204 can include a concave curved surface, or include curved surface portions that directly impinge with the fluid stream from the nozzle 124. In one example, the curved chamber walls 204 include a curvilinear cross section in the plane of the fluid stream. Curved chamber walls 204 or portions of curved chamber walls 204 can include a set of adjacent, angled linear walls configured to approximate a curved shape. In one example, the curved chamber walls 204 may form a concave spherical, or bowl shape as in the interior of a sphere or a concave parabolic shape such as a parabolic collector. In another example, the curved chamber walls 204 may generally conform to a parabolic cylinder, similar to a parabolic trough, which includes parabolic cross section in a plane of two orthogonal coordinates but is generally linear along the third orthogonal coordinate. Other examples can include curved chamber walls 204 forming a portion of a cylinder or an elliptical cylinder. In still other examples, the curvilinear chamber walls 204 may approximate the interiors of cylinders, spheres, parabolic cylinders, elliptical cylinders, or parabolas. In one example, the chamber walls 204 may form a symmetrical chamber 202 about an axis or plane, in the case of a curved cylinder, or may form an asymmetrical chamber 202.

The chamber walls 204 may be integrally formed into the denuder container 200 or, in some examples, be a separate piece that can be inserted into the denuder container. In one example, the waste opening 126 can be integrally formed into a container body, and the chamber walls may be inserted into and removed from the container body. The clinician may be able to select an appropriate chamber wall 204 to insert into the denuder container depending on the application or the amount of non-bone tissue to be removed from the bone stock.

The grate 206 can be formed as holes through at least a portion of the chamber walls 204 that extend into the redirection cavity 208. In another example, the grate 206 can include a screen or grill covering the redirection cavity 208 and forming a portion of the chamber wall 204. A waste opening 126 can be included in the chamber wall 204 to drain fluid and non-bone tissue from the wash chamber, the redirection channel wall 210 to drain fluid and non-bone tissue from the redirection channel 208, or both.

Figure 3:
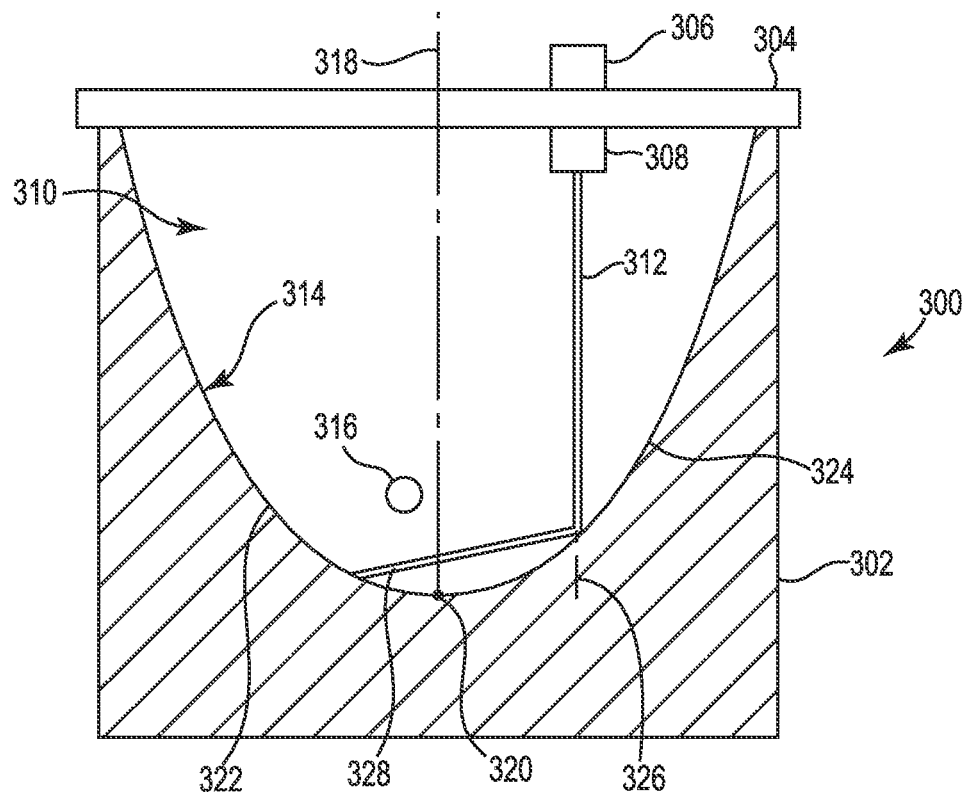
FIG. 3 is sectioned schematic view illustrating a portion of an example denuder container of FIG. 2.

FIG. 3 illustrates a first example of a denuder container 300, which may correspond with denuder container 102. The denuder container 300 includes a container body 302 and container cap 304. The example denuder container cap 304 includes a fitting 306 that is operably coupleable to tube, such as tube 110 and a nozzle 308, which can correspond with nozzle 124, that is fluidically coupleable to a source of fluid, such as fluid source 104. The container cap 304 is removably attached to the container body 302 in the example to provide a fluid-tight, or generally fluid-tight seal.

The denuder container 300 includes an internal wash chamber 310 into which a bone stock can be received and the nozzle 308 can direct a stream of fluid, as depicted by fluid stream 312. Chamber walls 314 in the container body 302 form the example concave wash chamber 310. In the example, the chamber walls 314 include a waste opening 316 to drain fluid and non-bone tissue during denuding. The chamber walls 314 in the example have a curved surface and configured to form a parabolic wash chamber 310. The parabolic wash chamber 310 may include chamber walls 314 shaped as a paraboloid or approximately a paraboloid including a generally concave spherical lower section. The wash chamber 310 can include an axis 318, which may be an axis of symmetry. The axis 318 intersects the chamber walls 314 at a vertex 320, or the deepest point in the example wash chamber 310. The chamber walls 314 can include a first side 322 and a second side 324 for illustration. In one example, the chamber walls 314 can be fully symmetrical about the axis 318 and the wash chamber 310 may be an elliptical, or circular, paraboloid such as a parabolic cup or parabolic reflector. In another example, the first and second sides 322, 324 are symmetrical about the axis 318 and the wash chamber 310 may be a formed as a parabolic cylinder. In the example container 300, the chamber walls 314 are solid and generally fluid tight with the exception of the waste opening 316. The chamber walls 314 are illustrated as smooth in the example, but can include convex or concave ridges. In one example, the curved chamber walls 314 include a curvilinear cross section in the plane of the axis 318 as indicated in FIG. 3.

Fluid stream 312 enters the wash chamber 310 via nozzle 308 and is directed at the chamber wall 314 such as along a stream axis 326. The stream axis 326 can be distinct from the axis 318. For example, the stream axis 326 can be generally parallel to the axis 318, as illustrated, or at an angle to the axis 318. In the example, the fluid stream 312 impacts the chamber wall 314 at a location other than the vertex 320. The fluid is redirected after impact such as along redirection stream 328. In this example, the fluid stream 312, redirection stream 328, other redirected streams as well as subsequent redirection streams serve to cause the bone stock to tumble and the high pressure streams including fluid stream 312 and redirection stream 328 cause the non-bone tissue to separate from the bone. In another example in which the stream axis coincides with the axis 318 and the fluid stream impacts the chamber wall at the vertex 320, the bone stock tumbles away from the vertex as a result of impact with the stream but returns to the vertex 320 under the force of gravity.

Figure 4:
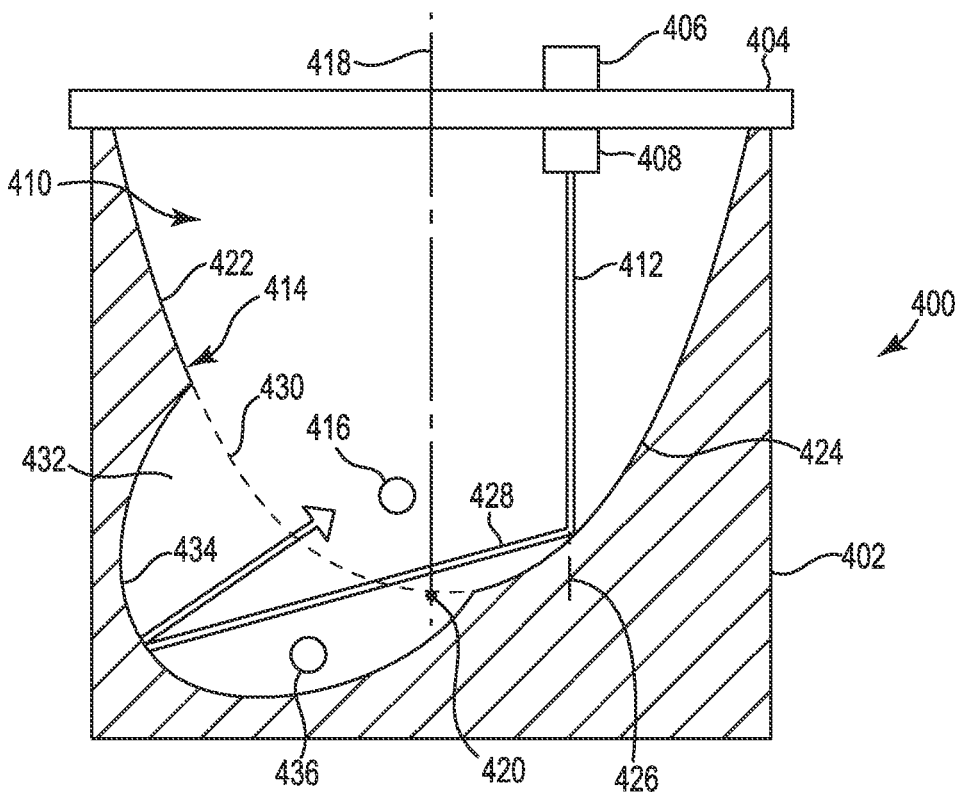
FIG. 4 is sectioned schematic view illustrating a portion of another example denuder container of FIG. 2.

FIG. 4 illustrates a second example of a denuder container 400, which may correspond with denuder container 102. The denuder container 400 includes a container body 402 and container cap 404. The example denuder container cap 404 includes a fitting 406 that is operably coupleable to tube, such as tube 110 and a nozzle 408, which can correspond with nozzle 124, that is fluidically coupleable to a source of fluid, such as fluid source 104. The container cap 404 is removably attached to the container body 402 in the example to provide a fluid-tight, or generally fluid-tight seal.

The denuder container 400 includes an internal wash chamber 410 into which a bone stock can be received and the nozzle 408 can direct a stream of fluid, as depicted by fluid stream 412. Chamber walls 414 in the container body 402 form the example concave wash chamber 410. In the example, the chamber walls 414 include a waste opening 416 to drain fluid and non-bone tissue during denuding. The chamber walls 414 in the example are curved and configured to form a parabolic wash chamber 410. In one example, the curved chamber walls 414 include a curvilinear cross section in the plane of the fluid stream 412 as in FIG. 4. The parabolic wash chamber 410 may include chamber walls 414 shaped as a paraboloid or approximately a paraboloid including a generally concave spherical lower section. The wash chamber 410 can include an axis 418, which may be an axis of symmetry. The axis 418 intersects the chamber walls 414 at a vertex 420, or the deepest point in the example wash chamber 410. The chamber walls 414 can include a first side 422 and a second side 424 for illustration. In one example, the chamber walls 414 can be fully symmetrical about the axis 318 and the wash chamber 410 may be an elliptical, or circular, paraboloid such as a parabolic cup or parabolic reflector. In another example, the first and second sides 322, 324 are symmetrical about the axis 318 and the wash chamber 310 may be a formed as a parabolic cylinder.

In the example, a portion of the chamber walls 314, such as the first side 422 in the illustration, can include a grate 430 over a redirection chamber 432 formed with a redirection wall 434 in the container body 402. Fluid can pass through the grate 430 from the wash chamber 414 into the redirection chamber 432, and fluid can pass through the grate 430 from the redirection chamber 432 into the wash chamber 414. In some examples, another waste opening 436 can be formed in the redirection wall 434 to drain fluid and non-bone tissue from the container 400. The chamber walls 414 are illustrated as smooth in the example, but can include convex or concave ridges.

Fluid stream 412 enters the wash chamber 410 via nozzle 408 and is directed at the chamber wall 414 such as along a stream axis 426. The stream axis 426 can be distinct from the axis 418. For example, the stream axis 426 can be generally parallel to the axis 418, as illustrated, or at an angle to the axis 418. In the example, the fluid stream 412 impacts the chamber wall 414 at a location other than the grate 430. The fluid is redirected after impact such as along redirection stream 428 into the redirection chamber 432 where the fluid impact the redirection wall 434 or flows along side the redirection wall 434 and returns through the grate 430 to the wash chamber 414. In this example, the fluid stream 412, redirection stream 428, other redirected streams as well as subsequent redirection streams serve to cause the bone stock to tumble and the high pressure streams including fluid stream 412 and redirection stream 428 cause the non-bone tissue to separate from the bone.

Although the present disclosure has been described with reference to preferred embodiments, workers skilled in the art will recognize that changes can be made in form and detail without departing from the spirit and scope of the present disclosure.

What is claimed is:

1. A method of denuding bone stock, the method comprising:
   depositing the bone stock into a wash chamber formed with a curved chamber wall;
   impacting the bone stock with a stream of fluid under pressure to separate non-bone tissue from bone; and
   draining the fluid and non-bone tissue from the wash chamber.

2. The method of claim 1 wherein the curved chamber wall forms the wash chamber configured as a parabolic cylinder.

3. The method of claim 1 comprising impacting the bone stock with a redirection stream of the fluid from the stream of fluid to separate the non-bone tissue from bone.

4. The method of claim 3 wherein the redirection stream is provided from a redirection chamber in fluid communication with the wash chamber.

5. The method of claim 4 wherein a grate separates the wash chamber from the redirection chamber.

6. The method of claim 3 comprising impacting the stream of fluid against the curved chamber wall to form the redirection stream.

7. The method of claim 6 wherein the curved chamber wall includes a redirection wall, and the impacting the stream of fluid against the curved chamber wall to form the redirection stream includes impacting the stream of fluid against the redirection wall.

8. The method of claim 1 wherein the stream of fluid includes a sterile water or saline.

9. The method of claim 1 wherein the fluid includes an abrasive or detergent.

10. A method of denuding bone stock, the method comprising:
    depositing the bone stock into a container body having wash chamber formed with a curved chamber wall including a grate, the curved chamber wall forming a wash chamber and the grate covering a redirection chamber in the container body; and
    impacting the bone stock with a fluid stream under pressure to separate non-bone tissue from bone.

11. The method of claim 10 wherein the fluid stream passes through the grate into the redirection chamber.

12. The method of claim 11 wherein the fluid stream in the redirection chamber returns from the redirection chamber as a redirection stream.

13. The method of claim 12 comprising impacting the bone stock includes impacting the bone stock with the redirection stream.

14. The method of claim 10 comprising draining the fluid stream and non-bone tissue drain from the container.

15. The method of claim 14 wherein draining the fluid stream and non-bone tissue includes draining the fluid stream and non-bone tissue through the redirection chamber or the wash chamber.

16. The method of claim 10 comprising impacting the fluid stream against the curved chamber wall to form a redirection stream wherein impacting the bone stock includes impacting the bone stock with the redirection stream.

17. A method of denuding bone stock, comprising:
    providing a container body having curved chamber wall forming a wash chamber the wash chamber configured to receive a bone stock;
    directing a fluid stream into the wash chamber to impact the curved chamber wall and form a redirection stream; and
    impacting the bone stock with the redirection stream to separate non-bone tissue from bone.

18. The method of claim 17 wherein the curved chamber wall includes a grate and the grate covers a redirection chamber in the container body.

19. The method of claim 18 wherein the grate can hold the bone stock within the wash chamber and the fluid from the fluid stream can pass through the grate into the redirection chamber.

20. The method of claim 17 wherein the wash chamber configured as a parabolic cylinder.

* * * * *